United States Patent [19]

Felder et al.

[11] Patent Number: 5,710,271
[45] Date of Patent: Jan. 20, 1998

[54] PROCESS FOR THE PREPARATION AND SEPARATION OF DIASTEREOMERIC SALTS OF FOLINIC ACID

[75] Inventors: Ernst Felder; Giorgio Ripa; Carlo Distaso, all of Milan, Italy

[73] Assignee: Dibra S.p.A., Milan, Italy

[21] Appl. No.: 480,097

[22] Filed: Jun. 7, 1995

Related U.S. Application Data

[63] Continuation-in-part of Ser. No. 456,767, Jun. 1, 1995, Pat. No. 5,599,931.

[30] Foreign Application Priority Data

Jun. 8, 1994 [IT] Italy .................... MI94A1193

[51] Int. Cl.$^6$ ............................................. C07D 475/04
[52] U.S. Cl. ................................................ 544/258
[58] Field of Search ............................................ 544/258

[56] References Cited

U.S. PATENT DOCUMENTS

| | | | |
|---|---|---|---|
| 2,737,515 | 3/1956 | Brockman | 544/258 |
| 4,148,999 | 4/1979 | Temple et al. | 544/258 |
| 4,206,307 | 6/1980 | Temple et al. | 544/258 |
| 4,500,711 | 2/1985 | Wisowaty et al. | 544/258 |
| 5,010,194 | 4/1991 | Mueller | 544/258 |
| 5,239,074 | 8/1993 | Marazza et al. | 544/257 |
| 5,300,505 | 4/1994 | Mueller et al. | 544/251 |
| 5,382,581 | 1/1995 | Marazza | 544/258 |
| 5,446,156 | 8/1995 | Jequier | 544/258 |
| 5,489,684 | 2/1996 | Jequier | 544/258 |
| 5,599,931 | 2/1997 | Ripa et al. | 544/258 |

FOREIGN PATENT DOCUMENTS 93-17022 9/1993 WIPO.

*Primary Examiner*—Donald G. Daus
*Attorney, Agent, or Firm*—Bucknam and Archer

[57] ABSTRACT

A process for the preparation, separation and purification of (6S) and (6R) diastereomers of folinic acid salts with at least dibasic amines is disclosed, which process comprises the hydrolysis of (6RS)-5,10-methenyl-5,6,7,8-tetrahydrofolic acid chloride hydrochloride with an at least dibasic amine and the subsequent separation of the diastereomeric salts.

7 Claims, No Drawings

PROCESS FOR THE PREPARATION AND SEPARATION OF DIASTEREOMERIC SALTS OF FOLINIC ACID

This application is a Continuation-in-Part of U.S. Ser. No. 08/456,767 filed Jun. 1, 1995 which has issued on Feb. 4, 1997 as U.S. Pat. No. 5,599,931.

This invention refers to a process for the preparation, separation and purification of stereoisomers of the salts of folinic acid which, in its calcium salt form, is used, in antitumoral therapy, as an antidote for the folic acid antagonists, such as antagonists of aminopterine or methotrexate. As a matter of fact, these substances block the metabolism of folic acid in the organism, preventing the transformation of dihydrofolic acid into tetrahydrofolic acid. On the contrary, in combination with another antitumoral drug, i.e. 5-fluoroacyl, calcium folinate increases the activity of folic acid. The folinic acid calcium salt is also used in all anaemic forms deriving from the lack of folates.

The process of the invention allows the preparation of the two diastereomeric forms of said salts in a convenient way, in good yields and with an high optical purity.

Folinic acid, N-(5-formyl-(6RS)-5,6,7,8-tetrahydropteroyl)-L-glutamic acid, when synthetically obtained, consists of the equimolar mixture of two diastereomeric forms, (6R) and (6S) respectively.

It is known that only the (6S) isomer, as calcium salt, meets the desired pharmacological activity: therefore processes allowing the preparation of said optically pure (6S) form have been extensively studied.

Several attempts were made to obtain the (6S) isomer through asymmetric synthesis [Rees L., Valente E., Suckling C. J., Wood H. C. S.—Tetrahedron Vol. 42—no. 1, pag. 117–136, 1986; Rees L., Suckling C. J., Wood H. C. S.—J. Chem. Soc., Chem. Commun., pag. 470–472, 1987; Brunner H., Huber C., Dublack P., EP551642-A1 (BASF-AG)], but none turned out to be industrially successful. Therefore most of the R&D work focused on the separation of the (6RS) diastereomeric mixture obtained by known synthetic ways, such as for instance, the one described by C. Temple and Coll. [U.S. Pat. No. 4,148,999; U.S. Pat. No. 4,206,307; J. Med. Chem. 22, 731 (1979)].

An example of the state of the art concerning said separation of (6R) and (6S) diastereomers from their equimolar mixture is given by the following list: U.S. Pat. No. 2,688,018; EP-A 0266042; EP-A 0348641; EP-A 0356934; EP-A 0367902; EP-A 0432441; EP-A 0455013; EP-A 0495204; WO 9113890; WO 8808844; WO 9317022.

The problem has not yet been solved as far as the industrial production is concerned, either related to the global yield, or to the optical purity of the obtained diastereomers.

This invention refers to a process which allows, starting from a known key intermediate, namely (6RS)-5,10-methenyl-5,6,7,8-tetrahydrofolic acid chloride hydrochloride [for instance obtained according to C. Temple; U.S. Pat. No. 4,148,999; U.S. Pat. No. 4,206,307; J. Med. Chem. 22, 731 (1979)], the preparation, separation and isolation of the diastereomeric salts of folinic acid with an at least dibasic organic amine, obtaining chemical and optical purity levels so high that the following transformation into the desired corresponding calcium salts is possible without performing further complex purification steps, providing therefore definite advantages from the industrial point of view.

As reported in Scheme 1, the folinic acid calcium salt is usually prepared starting from folic acid, which contains a (S) chiral centre in the part of the molecule corresponding to (S)-glutamic acid. By hydrogenation of the double bond between the 5- and 6-positions of the pterinic residue, a new chiral centre is formed in position 6 with a (6RS) configuration. The subsequent formylation of the nitrogen at the 5-position leads to the production of (6RS)-5,10-methenyl-5,6,7,8-tetrahydrofolic acid formate. By acidification with hydrochloric acid the crystallization of the corresponding chloride hydrochloride is obtained.

Scheme 1

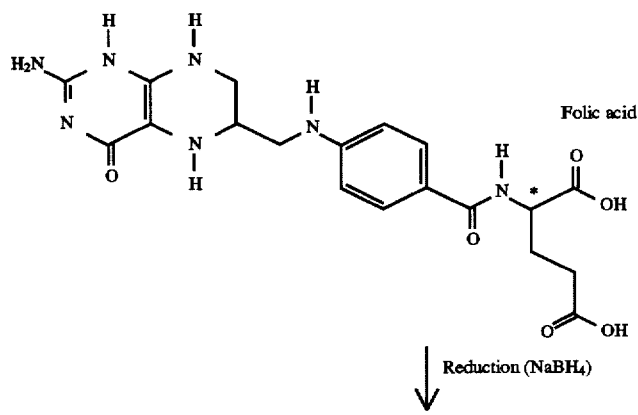

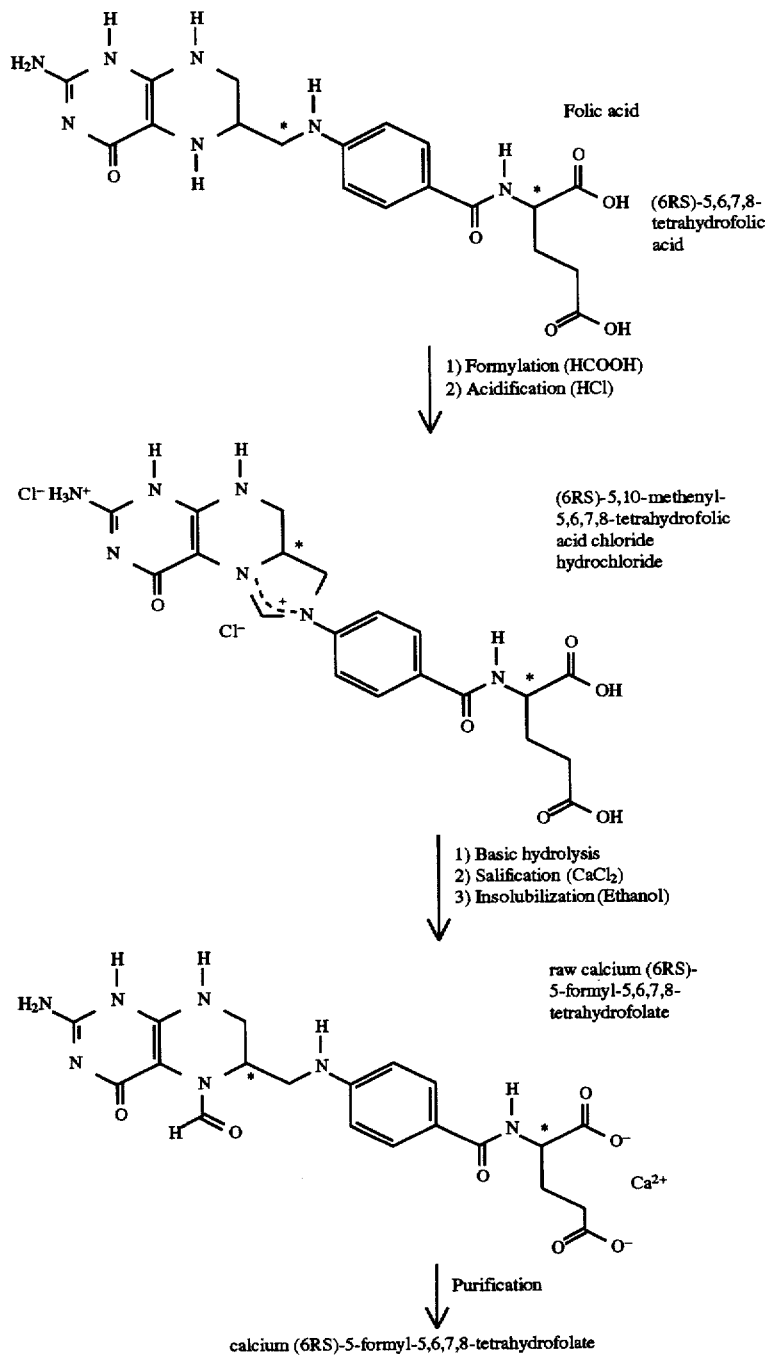

-continued
Scheme 1

This intermediate is hydrolyzed, preferably with strong inorganic bases (for instance NaOH), or with strongly basic organic monoamines such as triethylamine, and under strictly controlled pH conditions.

The mixture of diastereomeric salts of folinic acid is transformed into the mixture of the corresponding calcium salts (with $CaCl_2$). Said mixture is precipitated from ethanol to give (6RS) crude calcium folinate which is purified through various purification steps. By treating with acids an aqueous solution of purified (6RS) calcium folinate, (6RS) folinic acid precipitates which is ready for the diastereomeric separation.

The series of above disclosed operations is quite complex, especially due to the fact that the specificity of the reaction of hydrolysis of (6RS)-5,10-methenyl-5,6,7,8-tetrahydrofolic acid chloride hydrochloride is not very high; therefore a large number of impurities are produced causing a decrease in the reaction yield, so that the purification of calcium folinate has to be performed before carrying out the isolation of folinic acid and the subsequent separation of the diastereomers.

Now it has surprisingly been found that, in contrast to the prior art methods, said hydrolysis reaction can be performed in the presence of a suitable amount of a relatively weak base, consisting of an at least dibasic organic amine, which allows a high conversion and selectivity of the reaction. Moreover said diamine, in addition to its hydrolyzing function, acts at the same time as salifying agent for the folinic acid which has been formed.

As a consequence, the final crude solution, which contains the mixture of the diastereomeric diamine salts of (6RS)-folinic acid with diamine, can be directly used in order to selectively crystallize one of the two diastereomeric forms with an optical purity usually higher than 95%.

The type of diamine used highly affects the selectivity of the crystallization: for instance the (6S) diamine salt can be isolated first and then the corresponding (6R) form can be recovered from the crystallization mother liquors. For instance this occurs when piperazine is used as dibasic amine.

The opposed effect can equally be achieved. When ethylenediamine is used as a base, then the first isomer which crystallizes is the (6R) salt and the corresponding (6S) form can subsequently be recovered from mother liquors by a further crystallization.

The preferential crystallization of the less water-soluble diastereomeric salt from the crude solution of the hydrolysis reaction can be carried out according to known methods (WO 9317022, BRACCO). Preferably said solution is suitably diluted with solvents such as a dipolar aprotic solvent or an organic protic solvent or a mixture thereof, in order to promote the crystallization of the less water-soluble form.

Meanwhile, the removal of reaction impurities and side-products, remaining in solution, is obtained to such an extent that just one recrystallization of the diamine salt gives an optical purity higher than 99%.

In the most favourable cases, the optical and chemical purities of the diamino folinate diastereomer directly crystallized from the crude product deriving from hydrolysis are so high that they allow an easy conversion of said salt into the corresponding calcium salt without further purifications.

The stoichiometry of the hydrolysis reaction of (6RS)-5,10-methenyl-5,6,7,8-tetrahydrofolic acid chloride hydrochloride to diamine salt of folinic acid depends on the basicity of the amino groups of the used diamine.

For instance, ethylenediamine and 1,3-diamino-2-propanol are used in a 2:1 molar ratio to the starting product (i.e. in a stoichiometric ratio to the quantity of acid to be neutralized). For piperazine and N,N-dimethyl piperazine, less basic than the previous ones, a 3:1 molar ratio is preferred. Even in this case, the obtained diastereomeric salt consists of folinic acid and diamine in a 1:1 molar ratio, since each of the remaining two diamine moles neutralizes one equivalent of hydrochloric acid (for instance giving piperazine monohydrochloride).

Suitable at least dibasic organic amines may be selected from the group of aliphatic, linear, cyclic or heterocyclic, substituted or unsubstituted, racemic or optically active amines, containing at least two amino groups which are linked by at least a hydrocarbon chain, substituted or not, comprising at least 2 carbon atoms.

Particularly preferred amines are the diamines of the general formulae (I) to (III):

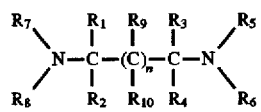 (I)

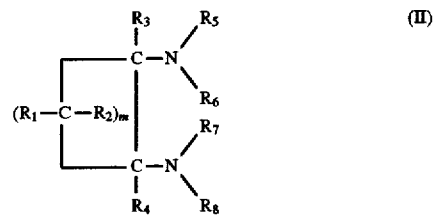

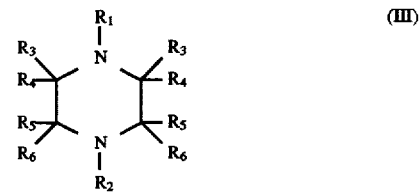

wherein:

$R_1 \rightarrow R_8$ which are the same or different, are H or a linear or branched alkyl group, substituted or not by 1–4 OH groups;

$R_9 \rightarrow R_{10}$ which are the same or different, have the same meanings as $R_1$–$R_8$ or represent hydroxy groups;

n is an integer from 0 to 6, m is an integer from 2 to 8.

Examples of particularly preferred amines are selected from: ethylenediamine, 1,2-diamino-propane, 1,3-diamino-propane, 1,3-diamino-2-hydroxy-propane, (cis)-1,2-diamino-cyclohexane, (trans)-1,2-diamino-cyclohexane, piperazine, 1,4-dimethyl-piperazine, 2-methyl-piperazine, 2,5-dimethylpiperazine.

Suitable solvents for the crystallization of diastereomeric mixtures of folinic acid salts with said amines are preferably binary or ternary mixtures of water/organic dipolar aprotic solvent or water/organic aprotic dipolar solvent/protic organic solvent.

Preferred aprotic dipolar solvents are, for example, dimethylformamide (DMF), dimethylacetamide (DMAC), dimethylsulfoxide (DMSO), N-methyl-pyrrolidone (NMP), hexamethylphosphoramide (HMPA).

Preferred organic protic solvents are methanol, ethanol, n-propanol, isopropanol, n-butanol, sec-butanol, ethylene glycol, 1,2-propylene glycol, 1,3-propylene glycol, formamide, N-methyl-formamide.

The process of this invention is described in the following Scheme 2 by using as starting products (6RS)-5,10-methenyl-5,6,7,8-tetrahydrofolic acid chloride hydrochloride, preferably prepared according to the procedure described by C. Temple [U.S. Pat. No. 4,148,999; U.S. Pat. No. 4,206,307; J. Med. Chem. 22, 731 (1979)], and, as an example of diamine, piperazine.

Scheme 2

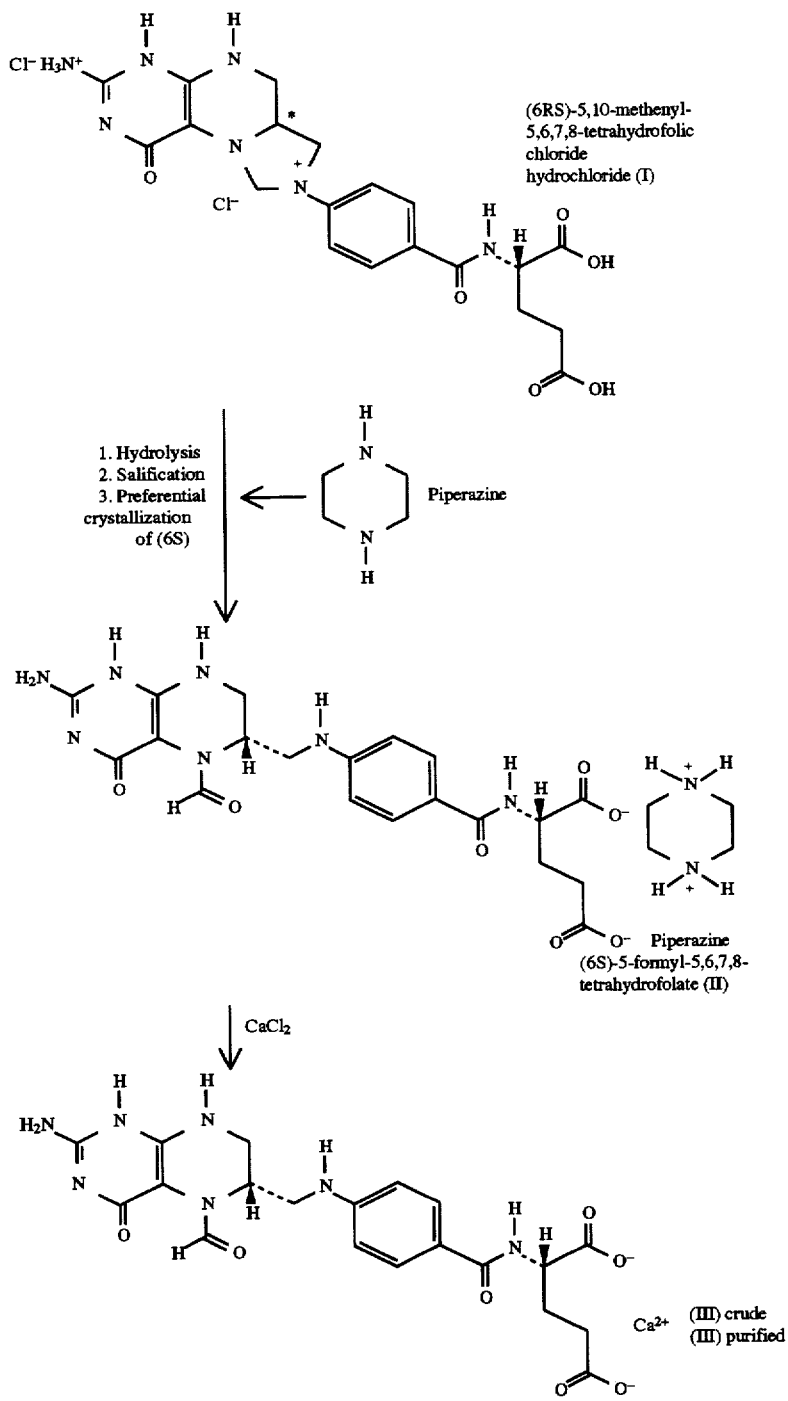

Hydrolysis of (6RS)-5,10-methenyl-5,6,7,8-tetrahydrofolic acid chloride hydrochloride.

The reaction is preferably performed under the following conditions:

acid/diamine molar ratio: from 1:2 to 1:4, preferably from 1:2 to 1:3.2 solvent: water or a water/aprotic dipolar solvent mixture (for instance DMAC) in a weight ratio from 1:0.5 to 1:20 acid/solvent mixture dilution ratio: from 1:2 to 1:80 w/w, preferably from 1:4 to 1:45 w/w temperature: from 60° to 100° C.

reaction time: from 3 to 12 h, preferably from 5 to 8 h.

The reaction is preferably performed under inert gas atmosphere. Preferential crystallization of the less water-soluble diastereomer of diamine folinate from the crude solution after hydrolysis.

The crude solution obtained once the hydrolysis reaction is over, is cooled and then treated according to one of the following methods:

possible further dilution with aprotic dipolar solvent (for instance DMAC) to increase the water/aprotic dipolar solvent ratio, preferably up to a maximum of 1:60 w/w.

if necessary, further addition of an organic protic solvent (for instance EtOH), preferably in order to reach a maximum weight 12 times higher than the solution weight.

The crystallization is generally carried out at temperatures ranging from 0° to 25° C. and for 10 to 120 h, preferably from 24 to 72 h. Transformation of the diamine salt into the corresponding calcium salt.

The exchange takes place in an aqueous solution in the presence of an excess of calcium salt (preferably $CaCl_2$) at a nearly neutral pH, preferably under the following conditions:

dilution ratio diamine salt/water: from 1:4 to 1:40 w/w preferably from 1:8 to 1:15 w/w diamine salt/$CaCl_2 \cdot 2H_2O$ ratio: from 1:1 to 1:6 w/w preferably from 1:3 to 1:5 w/w temperature: from 5° to 25° C.

crystallization time: from 10 to 60 h pH: between 6.5 and 7.5, if necessary with the addition of 1N NaOH.

From the residual mother liquors, if necessary after preferential crystallization of diamino folinate [respectively (6S) or (6R) according to the used diamine], even the other diastereomer can be recovered with an extremely high optical purity.

The preferred conditions are basically similar to those disclosed in WO 9317022 (BRACCO), and involve the crystallization of the diamine salt of the remaining diastereomer by dilution of mother liquors with a suitable solvent or solvent mixtures, its recrystallization and the subsequent transformation into the corresponding calcium salt.

Alternatively, the calcium salt can be obtained directly from the diamine salt in the starting mother liquors; recovery and purification can be carried out according to known methods (WO 9317022, BRACCO).

The following examples further illustrate the invention.

Example 1

Hydrolysis with piperazine and preferential crystallization of piperazine (6S)-folinate.

25 g of 5,10-methenyl-5,6,7,8-tetrahydrofolic acid chloride hydrochloride are suspended in 200 g of N,N-dimethylacetamide and in 49.0 g of water. The suspension is heated to 75° C., and 11.28 g of piperazine are added. The solution is heated to 80° C. and is kept at this temperature for 5 h. It is then diluted with 250 g of N,N-dimethylacetamide and cooled to 15° C. Crystallization occurs at 15° C. during 48 h. The crystallized solid is filtered, washed with 40 g of ethanol and dried. 9 g of piperazine (6S)-folinate with an optical purity higher than 98% are obtained.

Example 2

Conversion of piperazine (6S)-folinate into (6S)-calcium folinate.

8 g of piperazine (6S)-folinate, obtained according to example 1, are dissolved in 120 g of water. 32 g of calcium chloride dihydrate are added. pH is adjusted to 7 with 1N NaOH, then crystallization takes place at 16° C. in 24 h. The crystallized solid is filtered, washed with aqueous ethanol and dried. 6 g of (6S)-calcium folinate, with an optical purity higher than 99% are obtained. The product is dissolved again in water and reprecipitated by addition of ethanol. 5.7 g of (6S)-calcium folinate, with an optical purity higher than 99%, free from chloride ions, are obtained.

Example 3

Isolation of crude piperazine (6R) folinate from crystallization mother liquors of example 1.

270 g of ethanol are added to the mother liquors of example 1. The solution crystallizes at 5° C. in 64 h. The precipitated solid is then filtered off and washed with 40 g of ethanol. 8 g of piperazine (6R)-folinate with an optical purity higher than 90% are obtained.

Example 4

Preparation of piperazine (6R)-folinate with a high optical purity (>99%).

6 g of piperazine(6R)-folinate, obtained according to example 3, are dissolved at 50° C. in 20 g of water and 110 g of N,N-dimethylacetamide. After cooling the solution to 25° C., 20 g of ethanol are added and the solution is cooled to 5° C. The product crystallizes in 64 h at 5° C. The crystals are filtered, washed with ethanol and dried. 5.0 g of piperazine (6R)-folinate with an optical purity higher than 99% are obtained.

Example 5

Conversion of piperazine (6R)-folinate into (6R)-calcium folinate.

4 g of piperazine (6R)-folinate, obtained according to example 4, are dissolved in 20 g of water. 12 g of calcium chloride dihydrate, dissolved into 20 g of water, are added. pH is adjusted to 7 with 1N NaOH. 100 g of ethanol are added to precipitate (6R)-calcium folinate. 3.2 g of (6R)-calcium folinate with an optical purity higher than 99% are obtained.

Example 6

Hydrolysis with ethylenediamine and preferential crystallization of crude ethylenediamine (6R)-folinate.

30 g of 5,10-methenyl-5,6,7,8-tetrahydrofolic acid chloride hydrochloride are suspended in 176 g of water and 204 g of N,N-dimethylacetamide (DMAC). The suspension is heated to 80° C. and a solution of 6.3 g of ethylenediamine in 26.9 g of DMAC and 23.1 g of water is added dropwise in 3.5 h and kept under stirring at 80° C. for 5 h. The solution is cooled at 5° C. and left to stand for 24 h. The crystallized solid is filtered and washed with 15 g of ethanol, then dried. 10.3 g of ethylenediamine (6R)-folinate, 95.5% optically pure, are obtained.

Example 7

Isolation of ethylenediamine (6S)-folinate starting form mother liquors of example 6.

42.5 g of DMAC are added to the mother liquors of example 6. The solution is cooled to 10° C. and seeded with ethylenediamine (6S)-folinate. After 92 h, the crystallized solid is filtered, washed with 10 g of ethanol, then dried. 2.6 g of ethylenediamine (6S)-folinate, 99% optically pure, are obtained.

Example 8

Preparation of (6S)-calcium folinate starting from the mother liquors of example 6.

80 g of calcium chloride dihydrate are added to the mother liquors of example 6. After addition of 900 g of ethanol, the solution is kept under stirring for 30 min, the precipitate is filtered, and washed with 40 g of ethanol. The product is dried, then redissolved in water and reprecipitated at pH 7 by addition of ethanol. 16 g of (6S)-calcium folinate, 75% optically pure, are obtained. The product is recrystallized three times from water, at pH 7 and in the presence of ~4 parts by weight of calcium chloride dihydrate. After dissolution in water and precipitation with ethanol, 5 g of (6S)-calcium folinate, with an optical purity higher than 99%, are obtained.

Example 9

Preparation of ethylenediamine (6R)-folinate with high optical purity (>99%).

5 g of ethylenediamine(6R)-folinate, obtained according to example 6, are recrystallized from 100 g of water/N,N-dimethylacetamide 1:1,16 w/w. 4 g of ethylenediamine (6R)-folinate with an optical purity higher than 99% are obtained.

Example 10

Preparation of (6R)-calcium folinate. 3.5 g of ethylenediamine(6R)-folinate, obtained according to example 9, are dissolved in 20 g of water. A solution of 12 g of calcium chloride dihydrate in 15 g of water is added. pH is adjusted to 7 with 1N NaOH, and 50 g of ethanol are added to precipitate (6R)-calcium folinate. 3 g of (6R)-calcium folinate with an optical purity higher than 99%, are obtained.

Example 11

Hydrolysis with 1,3-diamino-2-propanol and preferential crystallization of 1,3-diamino-2-propanol (6R)-folinate.

30 g of 5,10-methenyl-5,6,7,8-tetrahydrofolic acid chloride hydrochloride are suspended in 100 g of water and 220 g of N,N-dimethylacetamide (DMAC). The suspension is heated to 80° C. then a solution of 9.5 g of 1,3-diamino-2-propanol in 80 g of water is added dropwise in 3.5 h. When the addition is over the solution is left at 80° C. for 5 h. After cooling to 5° C., crystallization occurs in 48 h. The crystallized product is filtered, washed with 15 g of ethanol, then dried. 9.5 g of 1,3-diamino-2-propanol (6R)-folinate with a 95% optical purity are obtained.

Example 12

Preparation of 1,3-diamino-2-propanol (6S)-folinate.

45 g of DMAC are added to the mother liquors of example 11. The solution is cooled to 5° C. and kept under stirring for 2 days, at 5° C. The crystallized product is filtered, washed with 5 g of ethanol, and dried. 2.5 g of 1,3-diamino-2-propanol (6S)-folinate with an optical purity higher than 98%, are obtained.

We claim:

1. A process for the preparation of essentially pure (6S) diastereoisomer of the calcium salt of folinic acid which comprises the steps of:

1) reacting the racemic mixture of (6RS) -5,10-methenyl-5,6,7,8-tetrahydrofolic acid chloride hydrochloride of formula (I)

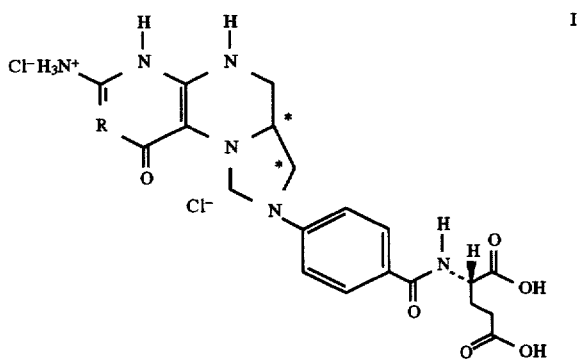

with a diamine which is a member selected from the group consisting of ethylenediamine, 1,2-diamino-propane, 1,3-diamino-propane, 1,3-diamino-2-hydroxy-propane, (cis)-1,2-diamino-cyclohexane, (trans)-1,2-diamino-cyclohexane, (trans)-1,2-diamino-cyclohexane, piperazine, 2-methyl-piperazine 1,4-dimethyl-piperazine, 2,5-dimethyl piperazine in a reaction medium which is water or a water/aprotic dipolar solvent mixture in a ratio of 1:05–1-20 by weight, said aprotic dipolar solvent being a member selected from the group consisting of dimethylformamide, dimethylacetamide, dimethylsulphoxide, N-methyl-pyrrolidone and hexa-methylfosphoramide; whereby said compound of formula (I) is hydrolyzed to give the racemic salt of (6 R,S) folinic acid with said diamine in a molar ratio of 1:1;

2) crystallizing the most insoluble diastereoisomeric salt of said amino (6 R,S) folinate by cooling the reaction solution from step 1) and adding an amount of said aprotic dipolar solvent up to a maximum water/aprotic dipolar solvent ratio of 1:60 by weight;

3) a) when in the most insoluble diastereoisomeric salt of step 2) is the (6S) diastereoisomer, reacting said amino (6S) folinate with calcium chloride in a (6S) salt/CaCl$_2$ ratio ranging from 1:1 to 1:6 by weight, in an aqueous solution, at a temperature from 5 to 25° C. and at a pH from 6.5 to 7.5;

b) when the most insoluble diastereoisomeric salt from step 2) is the (6 R) diastereoisomer, removing the same and then crystallizing the amino (6S) folinate from the mother liquors by adding one of the aprotic dipolar solvents of step 1) and finally treating said amino (6S) folinate with CaCl$_2$ as described in step 3 a) or directly treating said mother liquors with CaCl$_2$ as described in step 3 a).

2. The process according to claim 1 wherein in step 2) a polar protic solvent which is a member selected from the group consisting of methanol, ethanol, n-propanol, isopropanol, n-butanol, sec-butanol, ethylene glycol, 1,2-propylene glycol, 1,3-propylene glycol, formamide and N-methyl-formamide is added in an amount up to 12 times the weight of the solution.

3. The process according to claim 1 wherein step 1) is carried out in water as the only reaction medium.

4. The process according to claim 1 wherein in step 2) the crystallization of said most insoluble diastereoisomeric salt is carried out only by cooling the reaction solution from step 1) in the absence of additional solvents.

5. The process according to claim 1 wherein said diamine is piperazine in the molar ratio of 3:1 with respect to said racemic mixture of 5,10-methenyl-5,6,7,8-tetrahydrofolic acid chloride hydrochloride of formula (I) and the (6S) diastereoisomer of piperazine folinate is obtained in step 2) as the most insoluble product with a purity higher than 98%.

6. The process according to claim 1 wherein said diamine is ethylenediamine in the molar ratio of 2:1 with respect to said racemic mixture of 5,10-methenyl-5,6,7,8-tetrahydrofolic acid chloride hydrochloride of formula (I) and the (6S) diastereoisomer of ethylenediamine folinate is obtained from the mother liquor in step 3 b) after addition of dimethylacetamide.

7. The process according to claim 1 wherein said diamine is 1,3-diamino-2-propanol and said 6S diastereoisomer of 1,3-diamino-2-propanol folinate is obtained from the mother liquor in step 3 b) after addition of dimethylacetamide.

* * * * *